United States Patent [19]

Horowitz

[11] Patent Number: 4,815,449

[45] Date of Patent: Mar. 28, 1989

[54] DELIVERY SYSTEM FOR INTERSTITIAL RADIATION THERAPY INCLUDING SUBSTANTIALLY NON-DEFLECTING ELONGATED MEMBER

[76] Inventor: Bruce S. Horowitz, 16300 N. Park Pl., Southfield, Mich. 48075

[21] Appl. No.: 31,885

[22] Filed: Mar. 30, 1987

Related U.S. Application Data

[62] Division of Ser. No. 673,859, Nov. 21, 1984, Pat. No. 4,697,575.

[51] Int. Cl.⁴ .............................................. A61N 5/01
[52] U.S. Cl. ............................................. 600/7; 600/8
[58] Field of Search ............................. 128/1.1, 1.2

[56] References Cited

U.S. PATENT DOCUMENTS

| | | |
|---|---|---|
| 1,238,872 | 9/1917 | Bell . |
| 1,317,082 | 9/1919 | Hartenheim . |
| 1,494,826 | 5/1924 | Viol . |
| 1,517,861 | 12/1924 | Rosher . |
| 1,578,945 | 3/1986 | Withers . |
| 2,067,589 | 1/1937 | Antrim ................................ 47/1 |
| 2,153,889 | 4/1939 | Hames ............................ 128/1.1 |
| 2,322,902 | 6/1943 | Wappler ............................ 29/34 |
| 2,517,513 | 8/1950 | Vaernet ........................... 128/272 |
| 2,829,636 | 4/1958 | Henschke ........................ 128/1.2 |
| 3,127,313 | 3/1964 | Glenn ............................. 167/51 |
| 3,351,049 | 11/1967 | Lawrence ........................ 128/1.2 |
| 3,463,158 | 8/1969 | Schmitt et al. ................. 128/334 |
| 3,565,869 | 2/1971 | Prospero ........................ 260/78.3 |
| 3,589,356 | 6/1971 | Silverman ....................... 128/1.2 |
| 3,636,956 | 1/1972 | Schneider ...................... 128/335.5 |
| 3,663,685 | 5/1972 | Evans ............................... 424/1 |
| 3,750,653 | 8/1973 | Simon ............................. 128/1.2 |
| 3,867,190 | 2/1975 | Schmitt et al. ................. 117/138.8 |
| 3,872,856 | 3/1975 | Clayton .......................... 128/1.2 |
| 3,887,699 | 6/1975 | Yolles ............................. 424/19 |
| 3,927,325 | 12/1975 | Hungate et al. ................. 250/435 |
| 3,948,263 | 4/1976 | Drake, Jr. et al. .............. 128/260 |
| 3,950,282 | 4/1976 | Gilbert et al. .................. 260/9 |
| 3,976,071 | 8/1976 | Sadek ............................. 128/260 |
| 3,978,203 | 8/1976 | Wise .............................. 424/22 |
| 4,014,987 | 3/1977 | Heller et al. .................... 424/15 |
| 4,052,988 | 11/1977 | Doddi et al. ................... 128/335.5 |
| 4,054,138 | 10/1977 | Bucalo ........................... 128/260 |
| 4,086,914 | 5/1978 | Moore ............................ 128/1.2 |
| 4,096,239 | 6/1978 | Katz et al. ........................ 424/21 |
| 4,167,179 | 9/1979 | Kirsch ............................ 128/1.2 |
| 4,180,064 | 12/1979 | Heller et al. .................... 128/130 |
| 4,182,750 | 1/1980 | Sullivan et al. .................... 424/1 |
| 4,218,255 | 8/1980 | Bajpai et al. ..................... 106/45 |
| 4,249,531 | 2/1981 | Heller et al. .................... 128/260 |
| 4,304,767 | 12/1981 | Heller et al. ..................... 424/78 |
| 4,309,776 | 1/1982 | Berguer ............................... 3/1 |
| 4,322,398 | 3/1982 | Reiner et al. ..................... 424/19 |
| 4,323,055 | 4/1982 | Kubiatowicz ................... 128/1.2 |
| 4,351,337 | 10/1982 | Sidman .......................... 128/260 |
| 4,402,308 | 9/1983 | Scott ............................. 128/1.2 |
| 4,509,506 | 4/1985 | Windorski et al. .............. 128/1.2 |
| 4,510,924 | 4/1985 | Gray ............................. 128/1.2 |
| 4,534,760 | 8/1985 | Raible ............................ 604/175 |
| 4,588,395 | 5/1986 | Lemelson ........................ 604/59 |

FOREIGN PATENT DOCUMENTS

| | | |
|---|---|---|
| 30822 | 6/1981 | European Pat. Off. . |
| 64860 | 11/1982 | European Pat. Off. . |
| 2240746 | 3/1975 | France . |
| 24693 | of 1906 | United Kingdom . |
| 704628 | 2/1954 | United Kingdom . |

OTHER PUBLICATIONS

Vikram et al., "Non–Looping After Loading Technique for Interstitial Implants of the Base of the Tongue" Int. J. Radiation Oncology Biol. Phys., vol. 7, No. 3, pp. 419–422 (1981).

(List continued on next page.)

*Primary Examiner*—Max Hindenburg
*Assistant Examiner*—John C. Hanley
*Attorney, Agent, or Firm*—Robert C. Kain, Jr.

[57] ABSTRACT

A delivery system for interstitial radiation therapy comprising a substantially non-deflecting elongated member of material which is absorbable in living tissue and a plurality of radioactive seeds dispersed in a predetermined array within the member. In one form, the member comprises an elongated member having the seeds longitudinally spaced therein and forming a needle that can be inserted in the tumor to be treated.

6 Claims, 3 Drawing Sheets

OTHER PUBLICATIONS

Martinez et al., "Sterilization of 125I Seeds Encased in Vicryl Sutures For Permanent Interstitial Implantation", Int. J. Radiation Oncology Biol. Phys., vol. 5, No. 3, pp. 411–413 (1979).

Cunningham, Thy Physics of Radiology, 4th Ed., pp. 263–266 (1983).

3M Product Brochure I-125 Seeds in Carrier. Stamped Jul. 7, 1986.

"Radio Tags Bar Sponges in Patients", The Evening Star, p. A-20, Jul. 22, 1964.

M. Rotman et al., "Intracavitary Applicator in Relation to Complications of Pelvic Radiation" Int. J. Radiation Oncology Biol. Phys., vol. 4, pp. 951–956 (1978).

Blackshear, "Systems", Scientific American, pp. 66 et seq., Dec. 1979.

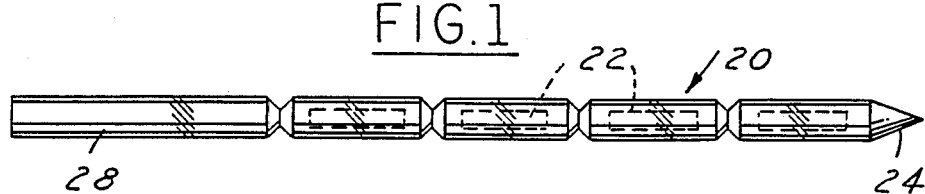
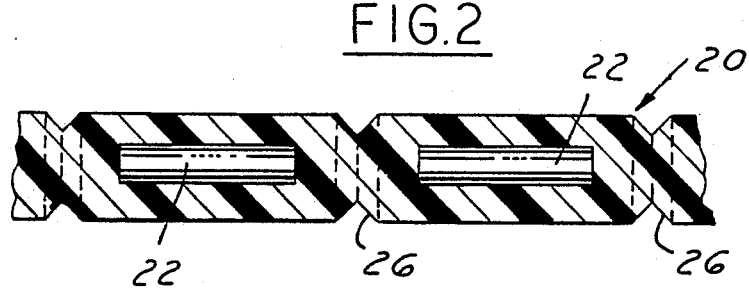
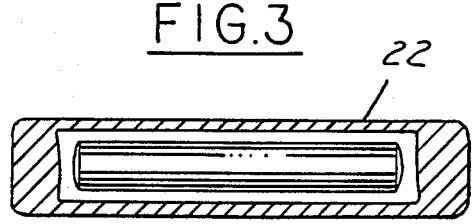
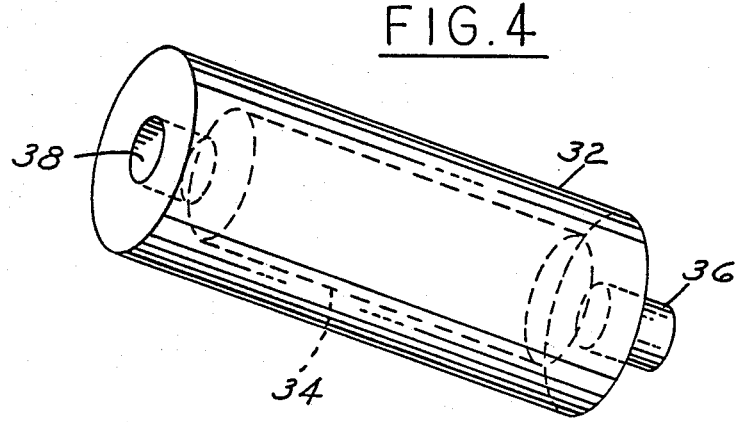

4,815,449

DELIVERY SYSTEM FOR INTERSTITIAL RADIATION THERAPY INCLUDING SUBSTANTIALLY NON-DEFLECTING ELONGATED MEMBER

This is a division of application Ser. No. 673,859 filed Nov. 21, 1984, U.S. Pat. No. 4,697,575.

This invention relates to brachytherapy and particularly to interstitial radiation and therapy and a delivery system for interstitial radiation therapy.

BACKGROUND AND SUMMARY OF THE INVENTION

Interstitial radiation therapy has been performed since the beginning of the 20th Century. Radium was developed by Madam Curie and Alexander Graham Bell proposed the use of radium in tumors. Subsequently, metal needles were developed in which a radium isotope was encapsulated for insertion in close proximity or into tumors. Where the tumor was deep seated, an operation was necessary to provide access to the tumor. Such therapy had serious problems and disadvantageous. The high energy of the radium isotope required a great deal of shielding and subjected the personnel to harmful exposure. In addition, the needles tended to break as they aged resulting in the release of the radioactive contents. Since the radium isotopes had a half-life of about 1600 years, they produced an extreme contamination hazard.

Thus, efforts have been made to develop more effective brachytherapy which is safer and more convenient to use. This has resulted in the development of radioactive materials that have lower energies and thus require less shielding and have shorter half-lives to reduce the risk of contamination. Thus, permanent seeds of encapsulated radon-222 having an energy level of 0.78 MEV and a half-life of 33.83 days or of encapsulated gold-198 having an energy level of 0.42 MEV and a half-life of 2.7 days have been used. More recently small seeds of iridium-192 having an energy level of 0.30 MEV and a half-life of 74.2 days and iodine-125 having an energy level of 0.028 MEV and a half-life of 60 days have been developed. Such seeds are shown, for example, in U.S. Pat. Nos. 3,351,049 and 4,323,055.

Such iridium and iodine seeds are on the order of 4.5 mm in length and 0.8 mm in diameter and are implanted in the tumor or placed in the surface of the tumor. Both of these sources have lower energies than radium that allow for simpler shielding and less radiation exposure to personnel. With seeds of iodine encapsulated in a material such as titanium, shielding is provided by the surrounding tissue and the seeds can be left in the patient permanently without the need for major precautions.

A further development in brachyterapy has been the development of techniques for handling the seeds. In one technique, hollow metal needles are inserted into the tumor and the seeds are thereafter inserted into the needles while the needles are being retracted to deposit the seeds in the tumor. Such devices are shown in U.S. Pat. No. 4,402,308. The most commonly used instruments are the Henschke and Mick devices. The spacing of the needles is determined by a nomograph developed by Drs. H. M. Kuam and L. L. Anderson of the Department of Medical Physics at Memorial Sloan-Kettering Cancer Center, New York, N.Y. The use of such devices has distinct disadvantages and problems. The overall length of such devices is over 20 cm and they have significant weight making them difficult to manipulate. Since the implant is performed through an open surgical wound, the needles can only be placed straight in a straight line or at an angle dictated by the relationship of the incision to the tumor. For example, the prostate is directly below the pubic bone with the incision being located cephalad. Since the prostate tends to rise behind the bladder, the preferred direction of the implant should be from a caudal approach, but this is not achievable using the available devices.

Another disadvantage of the above technique is that the seeds are deposited in a track made by the needle. When the needle is withdrawn, there is a tendency for the seeds to migrate in that track resulting in a poor distribution of the seeds. Because the energy levels are low (an exposure constant of 0.0184 for iodine-125 vs. $0.825^2 Rm^2 ci^1 h^1$ for radium), distribution between centers of adjacent seeds should be on the order of 1 cm. Poor distribution of seeds can result in undesirable concentrations of seeds resulting in either an overdosage or underdosage of radiation.

The seed is small because it needs to fit in small bore needles to prevent excessive tissue damage. The seed has a high seed surface dose and is difficult to handle because of its small size and can be easily lost and difficult to label.

In addition, the technique of implantation of individual seeds is time consuming.

In another technique that has been developed for treatment of tumors, plastic catheters are sutured on or in the tumor area and seeds placed in the catheters by insertion of a nylon tube carrying the seeds. After the desired treatment period, the nylon tubes are removed. The catheters are difficult to place so as to provide the proper dose distribution. It is also difficult to accurately space the catheters in parallel array over irregular surfaces and to anchor the catheters to the tissue. Irregular spacing can result in radiation overdose or underdose. Where the ends of the catheters are brought to the surface of the skin and sutured in place, there is an incipient source of contamination.

In another technique for treating tumors, seeds are initially placed by hand in a woven or braided absorbable carrier such as a braided suture. The carrier with the seeds laced therein is then secured in place to form a suitable implant. This technique is time consuming and may necessitate handling of the suture as well as having the same problems as to position and retention as the catheters. In order to minimize the radiation to personnel during handling and shipping, the suture with the seeds placed therein is shielded by placing it in a curved metallic tube. See European Patent Application Publication No. 0 064 860, published 17.11.82, Bulletin 82/46.

Accordingly, among the objectives of the present invention are to provide a delivery system which obviates the aforementioned disadvantages and allows placement of the seeds in accurate position to provide the desired interstitial radiation dose.

An object of the present invention is a delivery system for interstitial radiation therapy which is safer and easier to use than prior art systems. A further object of the present invention is a delivery system that causes a minimum of trauma to tissue. Yet another object of the present invention is a delivery system that allows for excellent control of the radiation dosage given the tissue. Still further objects of the present invention are a delivery system that can be used and placed with precision and a system that allows for improved accessability to tumors.

In accordance with the invention, the delivery system comprises a substantially non-deflecting member absorbable in living tissue. The member has a length that greatly exceeds its width or diameter. The non-deflecting member has a plurality of radioactive seeds dispersed therein in a predetermined array. In one form, the non-deflecting member comprises an elongated implant in the form of a needle for insertion in a tumor.

DESCRIPTION OF THE DRAWINGS

FIG. 1 is an enlarged side view of a delivery system in the form of a needle embodying the invention.

FIG. 2 is a greatly enlarged fragmentary sectional view on an enlarged scale of the needle shown in FIG. 1.

FIG. 3 is an enlarged sectional view of a typical seed utilized in the invention.

FIG. 4 is a greatly enlarged perspective view of a part of the needle shown in FIGS. 5 and 6.

DESCRIPTION

Figure 5:
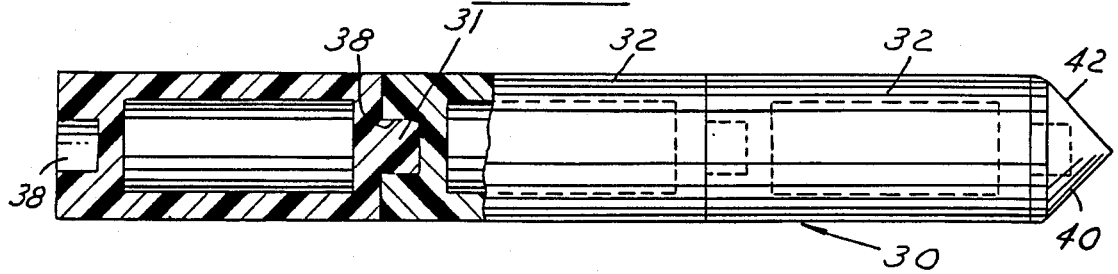
FIG. 5 is an enlarged part sectional view of a portion of the needle shown in FIG. 6.

In accordance with the invention, a substantially non-deflecting elongated member made of material which is absorbable in living tissue is provided preferably in the form of a needle or thin pointed cylinder for insertion in tumors. A plurality of radioactive seeds are encapsulated and positioned in a predetermined array in the body in the desired spaced relationships.

The seeds can be of various types having low energy and low half-life such as iodine seeds, known as I-125 seeds, consisting of a welded titanium capsule containing iodine 125 absorbed on a silver rod as shown in FIG. 3. Iridium seeds, designated Ir-192 seeds can also be used.

The non-deflecting elongated member may be made of any of the natural or synthetic absorbable materials. Examples of natural absorbable materials are the polyester amides from glycolic or lactic acids such as the polymers and copolymers of glycolide and lactide, polydioxanone and the like. Such polymeric materials are more fully described in U.S. Pat. Nos. 3,565,869, 3,636,956, 4,052,988 and European Patent Application No. 30822. Specific examples of absorbable polymeric materials that may be used to produce the substantially non-deflecting members of the present invention are polymers made by ETHICON, Inc., Somerville, N.J., under the trademarks "VICTYL" and "PDS".

The absorbable material should preferably maintain its integrity for from 1 to 14 days. Preferably the material should be absorbed in living tissue in a period of time of from about 70 to 120 days. It is preferred that as little absorbable material as possible be used in the delivery systems of the present invention.

In the form shown in FIGS. 1-3, the non-deflecting member comprises a needle 20 formed by an elongated plastic body in which the seeds 22 are encapsulated axially aligned in spaced relatioships. The needle has a tapered end 24 and a plurality of annular notches 26 are provided along the exterior surface in longitudinally spaced relation in the spaces between seeds so that the needle can be broken to provide the proper length dependent on the size of the tumor. In a typical case, the diameter of the needles is 1.06 mm.

The needles can be used in accordance with the following technique:

1. The tumor is exposed by a proper surgical technique. Alternatively, the tumor may be located by diagnostic methods using biplanar fluoroscopy, ultrasound or computerized tomography.

2. The size and shape of the tumor is determined.

3. The number of radioactive sources and spacing between the needles may be determined by the aforementioned nomograph technique developed by Drs. Kuam and Anderson. This calculation involves utilizing the average dimension and energy of the seeds as variables.

4. Each needle is inserted using one finger behind the tumor. When the end of the needle is felt bluntly, the proper depth has been reached.

5. Portions of the needles extending beyond the tumor are removed by breaking or cutting between or beyond the seeds.

6. After all the needles are in place, the surgical incision is closed, if the tumor has been exposed by surgical technique.

7. Dosimetry is monitored using stereo shift orthogonal radiographs and the appropriate computer program.

Figure 6:
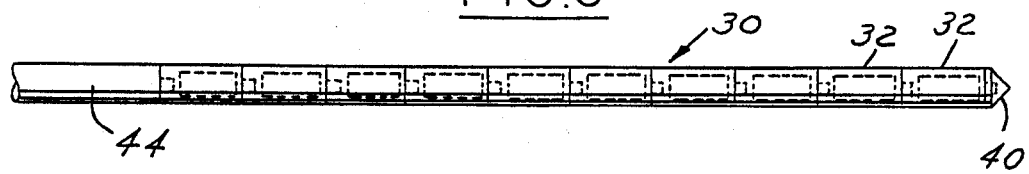
FIG. 6 is an enlarged view of a needle embodying the invention.
Figure 7:
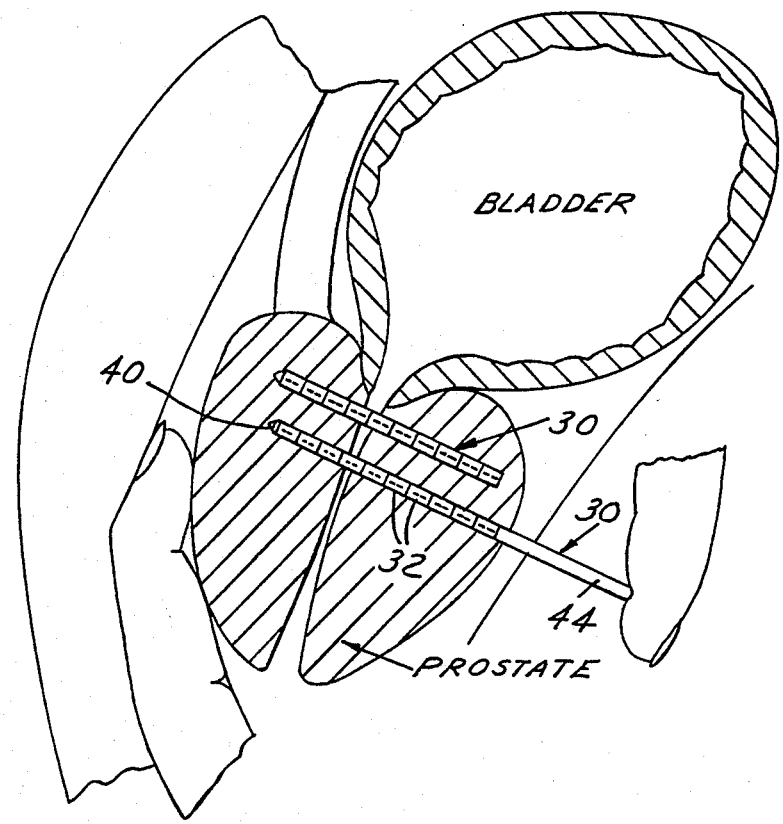
FIG. 7 is a diagrammatic view showing the manner of use of the needles embodying the invention.

In the form shown in FIGS. 4-6, the needle 30 is in the form of a member comprising a plurality of segments 32 of absorbable material, each of which encapsulates a seed 34 and the segments 32 are physically interconnected to form the needle. Each segment 32 is formed with an integral projection 36 at one end and a complementary recess 38 in the other end for engagement with the projection 36 of an adjacent segment 32. An endmost tapered segment 40 is provided to facilitate insertion in the tumor. The needle 30 facilitates selection of a needle of a proper length.

In each of the forms of needle heretofore described, a portion of the needle may be provided without seeds to form a handle 28 or 44 (as shown in FIGS. 1 and 6 respectively) for handling and insertion, which portion can thereafter be removed from the remainder of the needle which is left in the tumor.

Figure 8:
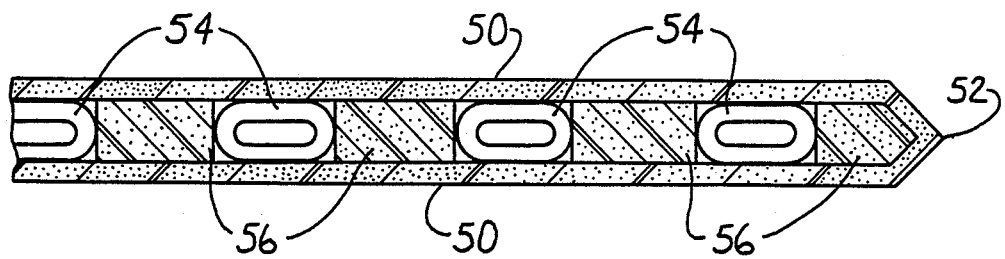
FIG. 8 is an enlarged side view of another embodiment of the delivery system of the present invention.

FIG. 8 shows another embodiment of a delivery system of the present invention. In this embodiment, a hollow tube 50 of absorbable material is used. One end of the tube is beveled or tapered to form an end for insertion of the tube in a tumor. Radioactive seeds 54 are spaced in the tube along its length. The seeds may be held in place in the tube by friction or if desired by spacers 56 of absorbable material between each seed as depicted in FIG. 8.

It is preferred the delivery system of the present invention be inserted directly into the tumor being treated by merely determining the desired location for the radioactive seeds and then inserting the substantially non-deflecting elongated member into the tumor in a pattern which will provide the desired location for the seeds. However, if desired, a suitable hollow metal needle or trocar may be inserted in the tumor to facilitate placement of the non-deflecting elongated member.

Though it is contemplated that the delivery system of the present invention may be inserted in tumors either with or without the assist of some insertion device, such as a hollow needle, the delivery system of the present invention should be substantially non-deflecting. By "non-deflecting" it is meant the delivery system has sufficient rigidity to be driven into a tumor without deflection to provide for controlled and precise placement of the radioactive material.

The rigidity or non-deflectability of the delivery system may be controlled be selection of the polymer used and dimensions of the delivery systems.

By making the delivery system substantially non-deflecting the system is self-guidable and is preferably used without any assisting device such as hollow needles. The placement and removal of hollow needles in the cancerous tumor may transfer cancer cells to healthy tissue which is undesirable. The new self-guiding delivery system of the present invention does not suffer from this deficiency.

The advantages of the improved delivery systems of the present invention are:

1. The substantially non-deflecting members provide access into tight areas and can be placed in the most suitable direction.
2. Fixed linear positioning of seeds to minimize "hot" and "cold" spots.
3. The normal tissue is spaced away from the seed surface by the thickness of the body of polymer to decrease necrosis from a high local dose.
4. Improved handling and labeling of the seeds that will reduce exposure and error.
5. Increased speed of implant resulting in reduced surgical time and personal exposure.

What is claimed is:

1. A delivery system for interstitial radiation therapy comprising:

an integral elongated member made from a material which is absorbable in living tissue, said member having a length substantially greater than its width, and a plurality of radioactive sources predeterminedly dispersed longitudinally in said member, said member having sufficient rigidity to be driven into a tumor without deflection to provide for controlled and precise placement of the radioactive sources in the tumor, said integral elongated member comprising:
a tapered tip at one end thereof; and,
a plurality of visibly identifiable and physically defined segments, a subgroup of said plurality of segments encasing said plurality of radioactive sources, each segment of said subgroup containing a corresponding radioactive source of said plurality of radioactive sources, said plurality of segments defining said integral elongated member with said tip at one end of said member.

2. The delivery system set forth in claim 1 wherein said elongated member is made from a copolymer of lactide and glycolide.

3. The delivery system set forth in claim 2 wherein said segments are delineated by circumferential grooves about said elongated member.

4. The delivery system for interstitial radiation therapy comprising: an elongated member made from a material which is absorbable in living tissue, said member having a length substantially greater than its width, and a plurality of discrete radioactive sources predeterminedly dispersed along the length of said member, said elongated member having sufficient rigidity to be driven into a tumor without deflection to provide for controlled and precise placement of the discrete radioactive sources in the tumor wherein said elongated member comprises a hollow tube of absorbable material having said plurality of discrete radioactive sources dispersed therein and longitudinally spaced therealong by a plurality of spacers of absorbable material disposed in said tube between one or more of said plurality of discrete radioactive sources to obtained a fixed linear positioning of all of said plurality of radioactive sources wherein said tube has a characteristic that maintains the tube's integrity and the fixed linear positioning at said plurality of radioactive sources for a first predetermined period of time subsequent to an implantation into said living tissue and wherein said tube has a further characteristic such that the tube is substantially absorbed by said living tissue over a second predetermined period of time that is longer than said first predetermined period of time.

5. The delivery system set forth in claim 4 wherein said hollow tube has a tapered end.

6. The delivery system set forth in claim 4 wherein each one of said plurality of discrete radioactive sources comprise a seed that defines an encapsulated discrete radioactive source.

* * * * *